US012557779B2

(12) United States Patent
Peiffer et al.

(10) Patent No.: US 12,557,779 B2
(45) Date of Patent: Feb. 24, 2026

(54) ANIMAL LITTER OR BEDDING CONTAINING CANNABIDIOL AND METHOD OF USE THEREOF

(71) Applicant: The Andersons Inc., Maumee, OH (US)

(72) Inventors: Norman A. Peiffer, Maumee, OH (US); Edward L. Sharek, Maumee, OH (US); Kevin L. McElfresh, Maumee, OH (US); Steven G. Myers, Maumee, OH (US); Jack T. Kimura, Maumee, OH (US)

(73) Assignee: The Andersons Inc., Maumee, OH (US)

( * ) Notice: Subject to any disclaimer, the term of this patent is extended or adjusted under 35 U.S.C. 154(b) by 1120 days.

(21) Appl. No.: 17/526,152

(22) Filed: Nov. 15, 2021

(65) Prior Publication Data

US 2022/0151196 A1     May 19, 2022

Related U.S. Application Data

(60) Provisional application No. 63/113,231, filed on Nov. 13, 2020.

(51) Int. Cl.
*A01K 1/015*      (2006.01)
*C07C 39/23*      (2006.01)

(52) U.S. Cl.
CPC ............ *A01K 1/0155* (2013.01); *C07C 39/23* (2013.01)

(58) Field of Classification Search
CPC .. A01K 1/0152; A01K 1/0154; A01K 1/0155; C07C 39/23
See application file for complete search history.

(56) References Cited

U.S. PATENT DOCUMENTS

| | | | |
|---|---|---|---|
| 2016/0346339 A1* | 12/2016 | Finley ................... | A61K 31/353 |
| 2018/0042890 A1* | 2/2018 | Sinai ....................... | A61K 45/06 |
| 2020/0061022 A1* | 2/2020 | Nowak ................. | A61K 9/1611 |
| 2021/0121403 A1* | 4/2021 | Niichel ................... | A61K 9/14 |

* cited by examiner

*Primary Examiner* — Brian A Mccaig

(74) *Attorney, Agent, or Firm* — MaxGoLaw PLLC

(57) ABSTRACT

An animal litter or bedding is provided that includes pieces adapted to be poured from a bag, that are in the form of a granule, shavings, shredded paper, or monolithic particles. A cannabidiol (CBD) oil coating or CBD containing plant tissue is provided in, or on a portion of the pieces. A method of treating hyperactivity or stress in a subject, such as a domesticated animal include contacting the subject to an animal litter or bedding and allowing sufficient time for the hyperactivity or stress to subside through the effect of the CBD oil on the subject.

19 Claims, No Drawings

ANIMAL LITTER OR BEDDING CONTAINING CANNABIDIOL AND METHOD OF USE THEREOF

RELATED APPLICATIONS

This application claims priority benefit of U.S. Provisional Application Ser. No. 63/113,231 filed Nov. 13, 2020; the contents of which are hereby incorporated by reference.

FIELD OF THE INVENTION

The invention in general relates to an animal litter and method of use thereof, and in particular to an animal litter or bedding and containing a cannabidiol (CBD) or a hemp plant containing CBD, and method of use thereof.

BACKGROUND OF THE INVENTION

The production of animal litter from various mineral and biomass granular materials is well known to the art. In other instances, wood shavings, shredded paper, or simply pieces of material with high surface area and limited dusting have been used as animal litter.

Animals living in confinement or as pets often experience high levels of stress associated with living conditions beyond their control such as temperature, lighting, and an inability to hide when insecure. They also experience a plethora of maladies illustratively including chronic pain, genetic disease, and infectious diseases. Elevated stress levels manifest in many ways illustratively including hyperactivity, aggression, anxiety, malaise, reduced appetite, increased appetite, self-harm, creation of "hot spots" due to excessive licking of the fur, and destruction of accessible items such as furniture in the case of a household pet. Conventional solutions for treating such ailments illustratively include the use of dietary supplements, prescription drugs, interactive toys or enclosure items, and the like. Such conventional solutions have been met with varying degrees of success. However, their effectiveness is largely dependent on a variety of factors unique to each animal, illustratively including specific affinity for interactive toys or enclosure items, willingness to ingest dietary supplements, and adverse reaction to prescription drugs. As such, the efficacy of conventional solutions remains inconsistent, and harmful side effects remain a risk. Furthermore, conventional solutions require the purchase of additional items not already required incident to caring for an animal living in confinement. Such treatments are only addressing the symptoms of the stress and fail to address the underlying stress.

The use of the cannabis plant for treatment of a wide range of conditions and diseases dates back millennia. Archaeological evidence suggests that cannabis was used by many ancient cultures including ancient Chinese, Indo-European, and Egyptian. Cannabinoid receptor type 1 (CB1) and cannabinoid receptor type 2 (CB2) are important signaling pathways for the endocannabinoid system. Psychoactive effects of cannabis are primarily mediated by CB1 which is primarily associated with the central nervous system, whereas CB2 is primarily associated with immune cells. THC has a high affinity for both CB1 and CB2. The high affinity for CB1 causes THC to be the primary psychoactive component of cannabis. In contrast, cannabidiol (CBD) which is a non-psychoactive cannabinoid component of the cannabis plant also known to be an effective treatment a variety of maladies illustratively including chronic pain, genetic and infectious disease, and stress, displays minimal affinity for both CB1 and CB2. Thus, CBD is a desirable compound that can be used to treat a variety of maladies without the risk of adverse psychoactive events inherent with the use of THC.

CBD acts as a partial CB1 antagonist and as a weak inverse CB2 agonist. CBD is also active at other receptors of the endocannabinoid system. Additionally, CBD is active at a variety of other molecular receptors that are not a part of the endocannabinoid system illustratively including agonism at serotonin 1A receptor, vanilloid receptor 1, and adenosine A2A receptors. CBD and has also been observed interacting with other biological systems via indirect chemical mechanisms. These characteristics are believed to play a role in the anti-inflammatory, pain, disease, and stress treating properties of CBD.

In addition to its anti-inflammatory properties, CBD does not cause the negative side effects caused by common compounds used to treat pain, disease, and stress. This makes it an even more attractive alternative for treating pain, disease, and stress over common prior art compounds currently in use. Yet, CBD has met with limited acceptance in treating pets owing to the need to dose the animal regularly and complications thereof.

Thus, there exists a need for an animal litter product that contains CBD. There further exists a need for an animal litter product that provides effective stress, disease, and pain treatment to animals living in captivity without the negative side effects caused by common compounds currently used in the art.

SUMMARY OF THE INVENTION

An animal litter or bedding is provided that includes pieces adapted to be poured from a bag, that are in the form of a granule, shavings, shredded paper, or monolithic particles. A cannabidiol (CBD) oil coating or CBD containing plant tissue is provided in, or on a portion of the pieces.

A method of treating hyperactivity or stress in a subject, such as a domesticated animal include contacting the subject to an animal litter or bedding. After a sufficient amount of time of exposure, the hyperactivity or stress subside through the effect of the CBD oil on the subject.

DETAILED DESCRIPTION OF THE INVENTION

The present invention has utility as an animal litter operative to absorb animal urine or an animal bedding. The present invention has further utility to treat hyperactivity experienced by animals living in captivity. The present invention has further utility to treat stress experienced by animals living in captivity. In inventive embodiments, the present invention has even further utility to treat pain, genetic disease, infectious disease, or combinations thereof in animals living in captivity. By inclusion of CBD in an animal litter, the animal is exposed to CBD through a combination of dermal contact, ingestion through grooming, allogrooming, and aromatherapy.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

It is to be understood that in instances where a range of values are provided that the range is intended to encompass not only the end point values of the range but also intermediate values of the range as explicitly being included within the range and varying by the last significant figure of the range. By way of example, a recited range of from 1 to 4 is intended to include 1-2, 1-3, 2-4, 3-4, and 1-4. By way of further example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

Unless specifically stated or obvious from context, as used herein, the term "or" is understood to be inclusive. Unless specifically stated or obvious from context, as used herein, the terms "a," "an," and "the" are understood to be singular or plural.

Also, as used herein, "and/or" refers to and encompasses any and all possible combinations of one or more of the associated listed items, as well as the lack of combinations when interpreted in the alternative ("or").

The suffix "(s)" as used herein is intended to include both the singular and the plural of the term that it modifies, thereby including one or more of that term.

Reference throughout the specification to "one embodiment", "another embodiment", "an embodiment", and so forth, when present, means that a particular element (e.g., feature, structure, and/or characteristic) described in connection with the embodiment is included in at least one embodiment described herein, and may or may not be present in other embodiments. In addition, it is to be understood that the described elements may be combined in any suitable combination.

The present invention will now be described with reference to the following embodiments. As is apparent by these descriptions, this invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment may be deleted from the embodiment. In addition, numerous variations and additions to the embodiments suggested herein will be apparent to those skilled in the art in light of the instant disclosure, which do not depart from the instant invention. Hence, the following specification is intended to illustrate some particular embodiments of the invention, and not to exhaustively specify all permutations, combinations, and variations thereof.

According to the present invention, an animal litter is provided that includes pieces of material that can absorb animal urine and is only limited to compatibility with CBD. The pieces of material can be pouring from a bag as a free-flowing powder. It is appreciated that inventive compositions are also operative as animal bedding.

Feedstock pieces for a base animal litter operative herein are recognized to include those conventional to the art. Representative non-mineral feedstock pieces operative in the present invention illustratively include corncob; crushed hemp seed; cellulosic plant stalks; plant stocks; cellulosic plant husks such as coconut, psyllium, and corn; cellulosic plant hulls such as grain hulls, nut hulls, sunflower hulls, oat hulls, spelt hulls, soy hulls, and rice hulls; beeswing wheat bran; tree bark; fronds; miscanthus; grasses; straw; saw dust; wood shavings; kenaf; and finely divided granules of any of the aforementioned that are then agglomerated to form a piece of litter, and combinations thereof. In some inventive embodiments, the pieces are corncob granules that are held together with a binder. Representative mineral feedstock particulates operative in the present invention illustratively include dolomite, zeolite, perlite, diatomaeceous earth, Fuller's earth, bentonite, attapulgite; montmorillonite, cleosite, granite, gypsum, aluminum sulfate, vermiculite, and combinations thereof.

Milling a feedstock to pieces of granules is readily accomplished with a commercially available milling machine, hammer mill, pin mill, knife mill, air mill, cryogenic mill, or pulverizer. A Champion hammer milling machine (Waterloo, Iowa) is representative of such a milling machine. The milled granular feedstock desired to be agglomerated into a piece is then directed to a pan agglomerator in concert with a binder. Agglomerated pellet milling is also operative herein. The milled granular feedstock is delivered to the pan agglomerator by way of a conventional conveyance system that lessens dust production. Upon mixing the milled granule feedstock with a binder achieves a granule size where 90% by weight or more of the granules are between −5 and +60 screen sieve.

Alternatively, the milled granular feedstock is delivered to an extruder operating with at least one suitably sized die opening. The extruded rod of feedstock is cut into cylindrical granules and dried to achieve a desired granule size where 90% by weight or more of the granules are between −5 and +60 screen sieve.

The binder is present in amounts ranging from 0.5% to 95% by weight of the total dry weight of the litter. Illustrative examples of binders operative herein are carbohydrates such as monosaccharides, disaccharides, oligosaccharides and polysaccharides; proteins; lipids; glycolipid; glycoprotein; lipoprotein; and combinations and derivatives of these. Specific carbohydrate binders illustratively include glucose, mannose, fructose, galactose, sucrose, lactose, maltose, xylose, arabinose, trehalose and mixtures thereof such as corn syrup; celluloses such as carboxymethylcellulose, ethylcellulose, hydroxyethylcellulose, hydroxy-methylethyl-cellulose, hydroxyethylpropylcellulose, methylhydroxy-ethyl-cellulose, methylcellulose; starches such as amylose, seagel, starch acetates, starch hydroxyethyl ethers, ionic starches, long-chain alkyl starches, dextrins, amine starches, phosphate starches, and dialdehyde starches; plant starches such as corn starch and potato starch; other carbohydrates such as pectin, amylopectin, xylan, glycogen, agar, alginic acid, phycocolloids, chitin, gum arabic, guar gum, gum karaya, gum tragacanth and locust bean gum; complex organic substances such as lignin and nitrolignin; derivatives of lignin such as lignosulfonate salts illustratively including calcium lignosulfonate and sodium lignosulfonate and complex carbohydrate-based compositions containing organic and inorganic ingredients such as molasses. Suitable protein binders illustratively include soy extract, zein, protamine, collagen, and casein. Binders operative herein also include synthetic organic polymers capable of promoting or producing cohesion of methylene urea oligomer fines and these illustratively include ethylene oxide polymers, polyacrylamides, polyacrylates, polyvinyl pyrrolidone, polyethylene glycol, polyvinyl alcohol, polyvinylmethyl ether, polyvinyl acrylates, polylactic acid, and latex. In a preferred embodiment, the binder is calcium lignosulfonate, molasses, a liquid corn starch, a liquid corn syrup or a combination thereof.

Conventional animal litters amenable to incorporation of CBD according to the present invention illustratively include those detailed in U.S. Pat. Nos. 6,053,125; 7,316, 201; 7,846,480; 8,496,966; and 10,051,834 of the assignee. Further illustrative examples of patented animal litters that may be amenable for use with the CBD oils of the present invention illustratively include the following non-exhaustive list: U.S. Pat. Nos. 3,675,625; 3,765,371; 3,916,831; 3,983, 842; 4,206,718; 4,258,660; 4,263,873; 4,355,593; 4,641, 605; 4,736,706; 4,957,063; 5,000,115; 5,097,799; 5,193, 489; 5,195,465; 5,207,389; 5,216,980; 5,267,532; 5,325, 816; 5,329,880; 5,458,091; 5,469,809; 5,735,232; 5,830, 765; 5,836,263; 5,856,024; 5,862,543; 5,884,584; 5,975, 019; 5,992,351; 6,029,603; 6,098,569; 6,019,062; 6,101, 978; 6,276,300; 6,371,049; 6,405,677; 6,622,658; 6,745, 720; 6,837,181; 6,895,896; 7,124,710; 7,331,309; 7,527, 019; 7,533,630; 7,665,418; 7,757,638; 8,156,896; 8,251, 016; 8,424,490; 8,522,720; 9,010,274; 9,119,374; and 9,232, 765.

Still other forms of animal litters include woods shavings that are particularly well suited for rodents, ruminates, and ungulates. Rolled paper as detailed in U.S. Pat. No. 9,398, 757 is also operative herein and particularly well suited for rodents and primates.

It is appreciated that various additives can be incorporated into a litter granule according to the present invention. These additives illustratively include a colorant, a fragrance, an acid neutralizing agent, and a desiccant. When present, a colorant or fragrance is typically present from 1 ppm to 10 dry weight percent of a granule. When present, an acid neutralizing agent is typically present from 0.05 to 10 dry weight percent of a granule. When present, a desiccant is typically present from 0.05 to 10 dry weight percent of a granule.

The resultant litter is then coated with CBD oil, incorporates hemp plant material containing CBD, or a combination thereof. The CBD oil is added to fully coat some or even all of pieces of litter. Typically, the CBD oil is added to the granules in an amount ranging from 0.001 to 5 total weight percent of litter and readily applied as a liquid by tumbling or by spray. Hemp plant material containing CBD is typically flaked or powdered aerial portions of the plant that have been dried. Typically, the CBD oil is added to the litter in a conventional fluidizing mixer; however, it is appreciated that there are a variety of conventional techniques by which granules can be coated by an oil according to the present invention. These techniques illustratively include spray coating and dip coating. In other embodiments, it is appreciated that in some inventive embodiments, crushed hemp seed provides the quantity of CBD oil as a surface decoration alone, or as pieces of the underlying granule to achieve the desired dosing of CBD. In some embodiments, the inventive animal litter or bedding includes hemp plant, hemp seed, or dried hemp plant material present from 1 to 99.5 total weight percent of the litter, or bedding.

Without intending to be bound to a particular theory, it is believed that the anti-inflammatory properties of CBD can be partially attributed to CBD being an agonist that targets CB2 receptors. Chronic inflammation can lead to chronic pain illustratively including arthritis. Suppressing or inhibiting inflammatory compounds can effectively treat chronic pain, genetic disease, and infectious disease. Without intending to be bound to a particular theory, it is believed that endocannabinoids play an active role the pathophysiology of chronic pain including imparting anti-inflammatory effects. It is further believed that the anti-inflammatory properties of CBD can also partially be attributed to CBD's ability to stimulate cannabinoid receptor activity and ability to enhance production and activity of endocannabinoids, catalyzing anti-inflammatory effects. By way of non-limiting example, it is believed that CBD stimulates production and enhances activity of the endogenous cannabinoid ligand anandamide—non-clinically known as the "bliss molecule"—because it reduces or prevents pain sensation. CBD has also been shown to modulate non-endocannabinoid signaling pathways illustratively including inhibition of adenosine uptake which provides increased protection against tissue damage during injury, and stimulation of enhanced activity at serotonin receptors. Without intending to be bound to a particular theory, it is further believed that the ability of CBD to stimulate enhanced activity at serotonin receptors and enhance activity of anandamide imparts anxiolytic stress and hyperactivity relieving properties, making CBD an effective treatment for stress and hyperactivity. CBD has also been shown to reduce NO production thereby reducing inflammation. CBD has further been shown to inhibit the expression of inflammatory cytokines and transcription factors. In contrast to other forms of delivery, the inventive litter transfers CBD to the hair of the animal and this creates a long term dermal exposure, while allogrooming and grooming through licking creates a secondary delivery mode through ingestion, and a tertiary mode of delivery is through CBD vapor as aromatherapy. The relative importance of these routes of delivery depending on the behavior of the animal. For example, ruminates and ungulates through standing contact with litter or in other contexts serves as bedding, absorb CBD through foot regions such as the coronet and pastern; while animals such as felines and rodents with regular fur-licking predominantly absorb CBD though ingestion.

In some inventive embodiments, the inventive animal litter includes a second oil on the litter pieces. In certain inventive embodiments, the second oil facilitates the subsequent adherence of a clumping agent. It is appreciated that according to various inventive embodiments, the second oil is applied prior to the CBD oil coating, after the CBD oil coating, as a diluent for the CBD oil, a coating on a hemp plant containing particle, or combinations thereof. In addition, the second oil is operative to lessen dust formation during subsequent handling, packaging, and usage. A second oil operative herein illustratively includes mineral oil, an essential oil, kerosene, vegetable oils, glycerin, paraffin distillates, naphthalene distillates, and combinations thereof. In some inventive embodiments, the second oil is added to fully coat the litter granules. Typically, the second oil is added to the granules in an amount ranging from 0.05 to 10 total weight percent of the litter or bedding. The second oil is applied by techniques used for the application of the CBD. In some inventive embodiments, the second oil coating includes an essential oil that is peppermint, spearmint, wintergreen, eucalyptus, rosemary, aloe, myrrh, frankincense, clove, lavender, orange blossom, chamomile, marjoram, yarrow, sandalwood, ginger, clary sage, juniper, cajuput, camphor, cinnamon, or combinations thereof. In other inventive embodiments, the CBD oil and the second oil are present in a weight ratio of from 0.1-5.0:1.

CBD oil coating present in the concentration range of the present invention appears to have synergistic effects with an essential oil. Still better results have been reported with the further administration of at least one of the aforementioned essential oils in combination with a cannabis or non-cannabis derived terpene added separate from the CBD oil. Again, without intending to be bound by a particular theory, it is believed that that oil phase plant extracts have vasodilation properties and solubility in the lipophilic myelin sheath surrounding inflamed nerve cells that interfere with nerve pain signaling.

In some inventive embodiments, the CBD oil also includes at least one terpene added separate from those found in the CBD oil. By way of reference CBD oil is found to contain in ever decreasing amounts: cannabidiol>myrcene>β-caryophyllene>(E)-β-ocimene. Terpenes added to an inventive composition illustratively include myrcene, limonene, linalool, menthol, humulene, terpinolene, camphene, terpineol, pinene, beta-caryophyllene, and combinations thereof. In some inventive embodiments, the at least one terpene is sourced from the cannabis plant. Terpenes are known to have a multitude of beneficial medical properties illustratively including anti-inflammatory, anxiolytic, muscle relaxant, analgesic, antibiotic, and antimutagenic properties. As such, the presence of at least one terpene into some embodiments of an inventive animal litter increases its efficacy in treating chronic pain, disease, and stress. An added terpene or combination thereof, if present, are present from 0.01 to 10 total weight percent of the plurality of sorbent granules.

By way of non-limiting example, humulene is anti-inflammatory, anti-bacterial, and anti-tumor, and β-caryophyllene is an agonist of CB2 and an anti-inflammatory. Humulene is commonly blended with β-caryophyllene which produces synergistic effects resulting in increased anti-inflammatory and pain treatment efficacy. Without intending to be bound by a particular theory, it is believed that β-caryophyllene, when coupled with CBD, produces increased activity at CB2 and also stimulates the increased production of endocannabinoids catalyzing an anti-inflammatory cascade that increases the efficacy of chronic pain treatment. An anxiolytic cascade is also believed to be catalyzed. In certain embodiments of an inventive animal litter or bedding, it is further believed that various terpene combinations, when blended with the CBD and various combinations of at least one essential oil, produce synergistic effects that result in increased anti-inflammatory and anxiolytic efficacy thereby increasing the efficacy of an inventive animal litter in treating chronic pain, disease, and stress upon contact with the skin of an animal.

In some embodiments, the inventive animal litter includes an additional active agent on the litter pieces. It is appreciated that according to various inventive embodiments, the additional active agent coating is lenabasum, CBD-Val-HS, EHP-101, EHP-102, KLS-13019, cannibigerol, or combinations thereof. Without intending to be bound by a particular theory, it is believed that the aforementioned impart further anti-inflammatory, anti-disease, and anxiolytic properties to the inventive animal litter, and also exhibit synergistic anti-inflammatory, anti-disease, and anxiolytic properties when combined with at least one of the aforementioned CBD oil coating, second oil, the at least one added terpene, or combinations thereof.

In some inventive embodiments, a clumping agent is adhered to the granule surface. A clumping agent according to the present invention is present as a particle decorating the surface of the litter granule. Clumping agents operative herein illustratively include gums such as guar, arabic, karaya, tragacanth and locust bean; celluloses such as corn syrup; celluloses such as carboxymethylcellulose, ethylcellulose, hydroxyethylcellulose, hydroxy-methylethylcellulose, hydroxyethylpropylcellulose, methylhydroxyethyl-cellulose, methylcellulose; starches such as amylose, seagel, starch acetates, starch hydroxyethyl ethers, ionic starches, long-chain alkyl starches, dextrins, amine starches, phosphates starches, and dialdehyde starches; plant starches such as corn starch and potato starch. Typically, the clumping agent is added in the range of 0.05 to 30 total weight percent relative of the litter.

It is appreciated that the clumping agent need not be present to attain an operative animal litter. Additionally, a clumping agent present at the lower ranges contemplated results in a more readily crumbled clump, whereas greater amounts of clumping agent tend towards rock-like clumps.

An inventive method for treating hyperactivity or stress in a subject is also provided and includes contacting to fur or skin of the subject an animal litter formed of pieces and a cannabidiol (CBD) oil coating on some or all the pieces, and allowing sufficient time for the hyperactivity or stress to subside.

In some inventive embodiments, the subject is a mammal including domesticated pets, captive animals, farm animals, and sporting animals. Specific animals include a cat, horse, cow, sheep, goat, llama, rodent, chicken, duck, turkey, monkey or chimpanzee. Exemplary rodents include a mouse, a rat, rabbit, a gerbil, guinea pig, or a hamster.

In certain inventive embodiments, it is appreciated that the inventive method also treats other maladies in addition to stress and hyperactivity illustratively including chronic pain, genetic disease, infectious disease, or combinations thereof.

EXAMPLES

Comparative Example

A cat litter base was made of a combination of dolomitic limestone and corn cob that is −40 mesh material to form base formula that is 75% white dolomite, 22% wood, and 3% starch binder, each by weight. To the base formula, the following was added 2% guar (−200 or −400) and 3% mineral oil.

Example 1

1 total weight percent of CBD and 0.2 total weight percent cedar fragrance are added to the Comparative Example with a corresponding reduction in white dolomite. Cats having feline interstitial cystitis, a chronic pain syndrome, under like living conditions showed reduced stress over five days as measure by vomiting of hair, food, or bile; diarrhea, soft feces, constipation; and skin lesions or chin acne using the litter of Example 1 relative to Comparative Example.

Example 2

The litter of Example 1 is modified to include 5 total percent by weight biochar for odor control with a commensurate reduction in wood. The resulting litter functions similar to the litter of Example 1.

Example 3

A cat litter based on −6 and +10 corn cob grit with 3% CBD is prepared. The resulting litter functions similar to the litter of Example 1.

Example 4

The cat litter of U.S. Pat. No. 10,051,834; Example 1 is modified to include 10 total weight percent of pressed hemp seed with a commensurate reduction in aerated concrete. The resulting litter functions similar to the litter of Example 1.

Example 5

The cat litter of U.S. Pat. No. 6,405,677; Example 1 is modified to include 10 total weight percent of pressed hemp seed with a commensurate reduction in seed meal. The resulting litter functions similar to the litter of Example 1.

Example 6

The litter of Example 1 is modified to include 5 total percent by weight biochar for odor control with a commensurate reduction in wood. The resulting litter functions similar to the litter of Example 1.

Example 7

Wood shavings are sprayed with a vegetable oil solution containing 20 weight percent CBD to result in 1 total weight percent CBD. The resulting material is used in a breeding group of 8 mice and reduces stress as observed by a reduction in barbering.

Example 8

0.25 total weight percent of dried hemp plant containing 12% by weight CBD are added to the Comparative Example with a corresponding reduction in white dolomite. The resulting litter functions similar to the litter of Example 1.

Those patents mentioned herein are intended to be incorporated by reference to the same extent as if each individual patent was explicitly and individually incorporated by reference It is recognized that various modifications will become apparent to one of skill in the art upon reading the above specification. Those modifications that retain the spirit of the invention are intended to be encompassed by the appended claims. While particular embodiments have been described, alternatives, modifications, variations, improvements, and substantial equivalents that are or may be presently unforeseen may arise to applicants or others skilled in the art. Accordingly, the appended claims as filed and as they may be amended, are intended to embrace all such alternatives, modifications variations, improvements, and substantial equivalents. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient roadmap for implementing the exemplary embodiment or exemplary embodiments. It should be understood that various changes may be made in the function and arrangement of elements without departing from the scope as set forth in the appended claims and the legal equivalents thereof.

The invention claimed is:

1. An animal litter or bedding comprising:
   a plurality of pieces suitable for physical contact with an animal's feet or fur and adapted to be poured from a bag, each of plurality of pieces independently being a milled granule feedstock with a binder to yield granules comprising a granule particulate that is 90% by weight or more able to pass −20 screen sieve and the binder such that greater than 90% of said granules have a size of between −4 and +60 screen sieve, shavings, and shredded paper; and
   a cannabidiol (CBD) oil coating or CBD containing plant tissue in or on a portion of said plurality of pieces.

2. The animal litter or bedding of claim 1 wherein said granules are composed of corncob, crushed hemp seed, cellulosic plant stalks, cellulosic plant husks, cellulosic plant hulls, or a combination thereof.

3. The animal litter or bedding of claim 1 wherein said granules are a majority by weight of corncob.

4. The animal litter or bedding of claim 1 wherein said plurality of pieces are spherical in shape.

5. The animal litter or bedding of claim 1 wherein said plurality of pieces are dolomite, zeolite, perlite, diatomaceous earth, Fuller's earth, bentonite, attapulgite; montmorillonite, cleosite, granite, gypsum, aluminum sulfate, vermiculite, or a combination thereof.

6. The animal litter or bedding of claim 1 further comprising clumping agent particles decorating the surface of each of said plurality of pieces.

7. The animal litter or bedding of claim 6 wherein said clumping agent is gum of guar, arabic, karaya, tragacanth or locust bean; celluloses of corn syrup, carboxymethylcellulose, ethylcellulose, hydroxyethylcellulose, hydroxy-methylethylcellulose, hydroxyethylpropylcellulose, methylhydroxyethyl-cellulose, or methylcellulose; starches of amylose, seagel, starch acetates, starch hydroxyethyl ethers, ionic starches, long-chain alkyl starches, dextrins, amine starches, phosphates starches, or dialdehyde starches; plant starches of corn starch or potato starch, or combinations thereof.

8. The animal litter or bedding of claim 1 further comprising a second oil coating applied prior to the CBD oil coating when present, after the CBD oil coating when present, as a diluent for the CBD oil when present, as a coating on the CBD containing plant tissue when present, or combinations thereof.

9. The animal litter or bedding of claim 8 wherein said second oil coating is mineral oil, an essential oil, kerosene, paraffin distillates, glycerin, naphthalene distillates, or combinations thereof.

10. The animal litter or bedding of claim 1 wherein said CBD is present in an amount of from 0.001 to 5 total weight percent.

11. The animal litter or bedding of claim 1 wherein said CBD oil further comprises at least one terpene added as a separate component.

12. The animal litter or bedding of claim 11 wherein said at least one terpene is menthol, myrcene, limonene, linalool, humulene, terpinolene, camphene, terpineol, pinene, betacaryophyllene, or combinations thereof.

13. The animal litter or bedding of claim 1 further comprising an additional coating on each of said plurality of granules, said additional coating being lenabasum, CBD-Val-HS, EHP-101, EHP-102, KLS-13019, cannabigerol, or combinations thereof.

14. A method for treating stress in a subject comprising:

contacting the subject to an animal litter or bedding of claim 1; and allowing sufficient time for the stress to subside.

15. The method of claim 14 wherein the subject is a cat.

16. The method of claim 14 wherein the subject is poultry.

17. The method of claim 14 wherein the subject is an undulate, a ruminate, a rodent, or a primate.

18. The method of claim 14 wherein the contact is through skin contact and ingestion.

19. The method of claim 14 wherein the contact is through aromatherapy.

\* \* \* \* \*